(12) United States Patent
Sauer

(10) Patent No.: US 10,052,496 B2
(45) Date of Patent: Aug. 21, 2018

(54) PHOTONIC WEARABLE APPARATUS LIGHT THERAPY DELIVERY SYSTEM AND CONTROL SYSTEM

(71) Applicant: Adora Sauer, Highland Park, IL (US)

(72) Inventor: Adora Sauer, Highland Park, IL (US)

(73) Assignee: MEDISUN ORTHO LLC, Highland Park, IL (US)

( * ) Notice: Subject to any disclaimer, the term of this patent is extended or adjusted under 35 U.S.C. 154(b) by 210 days.

(21) Appl. No.: 15/185,470

(22) Filed: Jun. 17, 2016

(65) Prior Publication Data

US 2016/0367834 A1    Dec. 22, 2016

Related U.S. Application Data

(60) Provisional application No. 62/181,951, filed on Jun. 19, 2015.

(51) Int. Cl.
  *A61N 5/06*    (2006.01)
  *A61N 5/067*    (2006.01)

(52) U.S. Cl.
  CPC .......... *A61N 5/0616* (2013.01); *A61N 5/0618* (2013.01); *A61N 2005/063* (2013.01); *A61N 2005/067* (2013.01); *A61N 2005/0645* (2013.01); *A61N 2005/0651* (2013.01)

(58) Field of Classification Search
  CPC ............................ A61N 5/0616; A61N 5/0618
  USPC ............................................. 607/88, 90, 91
  See application file for complete search history.

(56) References Cited

U.S. PATENT DOCUMENTS

| | | | | |
|---|---|---|---|---|
| 2007/0208395 A1* | 9/2007 | Leclerc | ................ | A61N 5/0616 607/86 |
| 2015/0290470 A1* | 10/2015 | Tapper | ................ | A61N 5/0616 607/91 |

* cited by examiner

*Primary Examiner* — Michael Carey
(74) *Attorney, Agent, or Firm* — Justin Lampel

(57) ABSTRACT

A photonic apparatus made from a stretchable and flexible material is provided. The apparatus may be a garment is especially suitable for wearing. The garment provides a wearer with light therapy which replicates the beneficial natural light of the sun therein providing health benefits which may include treatment of various medical conditions. The light source may include light emitting diodes (LEDs), optical fibers or solid state light emitting chips, which may be contained in a removable light transmitting pouch within the interior of the apparatus, so that the light may be powered by an internal power source to provide freedom of movement during treatment. In an embodiment, the light source is housed within the pouch wherein the pouch itself may be removed from the interior of the apparatus to be charged and replaced in the apparatus for wireless treatment use.

11 Claims, 6 Drawing Sheets

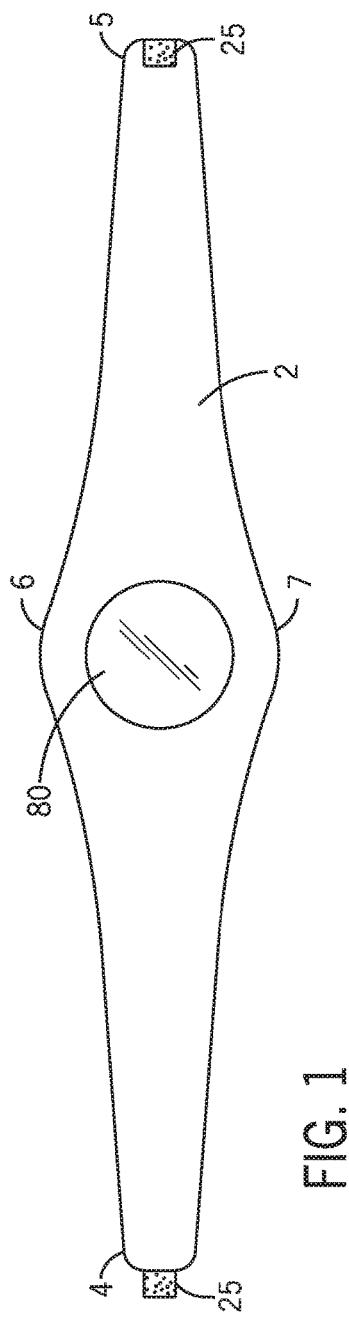
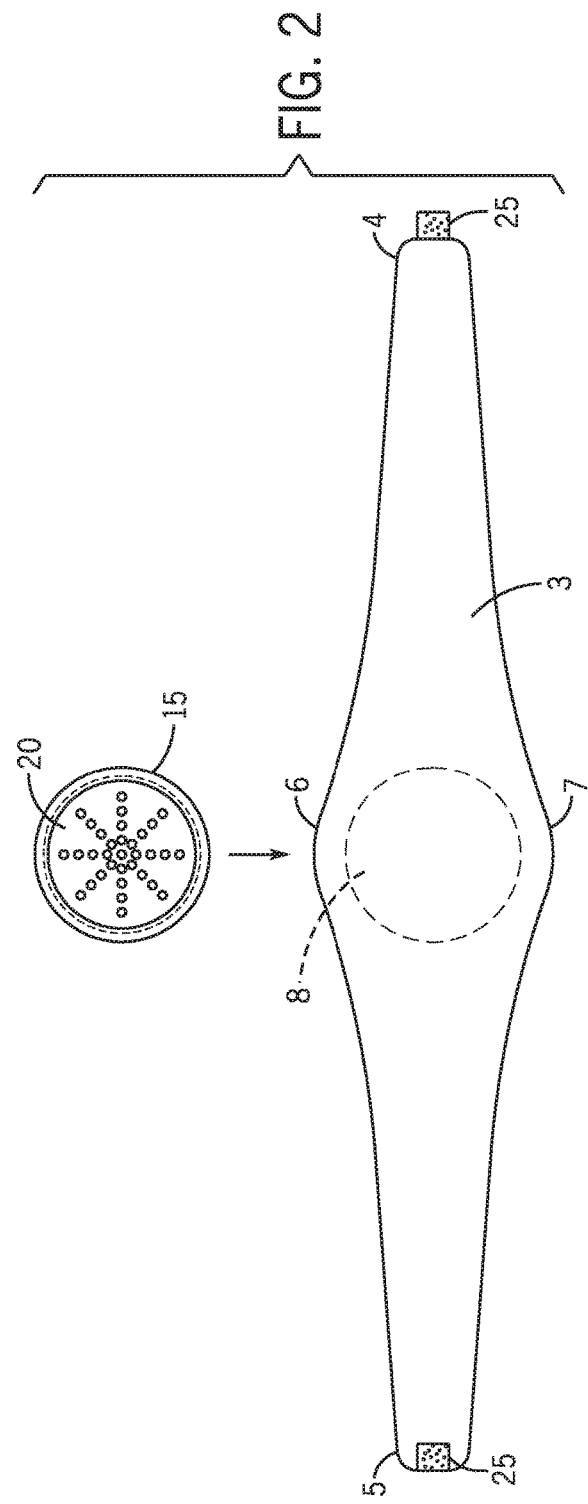

PHOTONIC WEARABLE APPARATUS LIGHT THERAPY DELIVERY SYSTEM AND CONTROL SYSTEM

CROSS REFERENCE TO RELATED APPLICATION

The following application is a based on and claims the priority benefit of U.S. Provisional Application Ser. No. 62/181,951 filed on Jun. 19, 2015; the entire contents of which are incorporated by reference.

BACKGROUND

A photonic apparatus made from a stretchable and flexible material is provided. The apparatus may be a garment is especially suitable for wearing around, for example, the torso of a person. The garment provides a wearer with light therapy within a specific wavelength range, which replicates the beneficial natural light of the sun therein providing health benefits that may include treatment of various medical conditions. The garment may take the form of a blanket, wrap, belt, cape, vest, hood, cap, headband, shirt or the like. The light source may include light emitting diodes (LEDs), optical fibers or solid-state light emitting chips, which may be contained in a removable light transmitting pouch within the interior of the apparatus, so that the light may be powered by an internal power source to provide freedom of movement during treatment. In an embodiment, the light source is removably housed within the pouch wherein the pouch itself may be removed from the interior of the apparatus to be charged and replaced in the apparatus for wireless treatment use.

Sunlight has been used as therapy dating back to ancient times. Noted historian from the 5th century B.C, Herodotus, chronicled the practice of using the sun for its health properties. The father of modern medicine, Hippocrates, recognized the benefits of the sun and treated all of his wearers with sunlight in a solarium.

The invention of artificial sunlight was brought to notoriety when Dr. Niels Finsen won the Nobel Prize for Medicine in 1903 for curing skin tuberculosis with ultraviolet light generated by mercury lamps. Since then, light therapy has been used for the treatment of many conditions including ill health, mood disorders and skin conditions. Widespread benefits for over 165 illnesses have been shown by safe controlled sun, UVB exposure, red and infrared light therapy including: enhanced mood and energy, skin issues such as acne and psoriasis, lowered blood pressure, decreased cholesterol, pain relief, infections like the flu and the common cold.

Light therapy has also been shown to reduce the risk of chronic illnesses such as cancer, cardiovascular disease, diabetes, high blood pressure, rheumatoid arthritis, autoimmune disorders, neurological disorders such as pain, traumatic brain injury, concussion, MS, Parkinson's disease and Alzheimer's disease. Phototherapy is currently also used extensively for treatment of skin disorders and bilirubin in infants. Low ultraviolet light exposure has been correlated to an increased risk for many conditions. Seasonal Affective Disorder is a mood disorder caused by decreased exposure to the sun, which affects over five hundred thousand Americans. Prevalent neurological disorders are also correlated with low UVB exposure such as Parkinson's effecting one million Americans, multiple sclerosis effecting two million Americans, and Alzheimer's effecting over five million people in the U.S. Sun and certain wavelengths of light exposure have also been shown to aid in the treatment and prevention of pain, traumatic brain injury, and concussion, which have become leading causes of death worldwide. Additionally, in the largest study of its kind, the sun exposure habits of thirty thousand women was examined over twenty years in Sweden and sun avoidance was found to be inversely correlated with all-cause mortality, which led researchers to conclude that sun avoidance was a risk factor for all causes of death.

Current light therapy devices on the market often produce beneficial wavelengths through mercury, halide, or fluorescent lamps. Providing phototherapy utilizing these large lamps requires large amounts of energy that usually creates tremendous heat and restricts the device from being portable. Additionally, the user must wear glasses and must stand at a specific distance from the lamps to utilize the energy effectively. The efficacy of these light therapy devices is dependent on wavelength, amount of surface area treated, and the distance of the light source to the skin. The present apparatus seeks to improve upon the current methods, apparatus and control systems for light therapy.

The present apparatus overcomes limitations of the prior phototherapy devices and creates a portable and wearable device that is beneficial for those with conditions treatable by light therapy, phototherapy, photo-modulation as well as people who may not have access to the sun due to geographical location, climate, and health reasons.

SUMMARY OF THE INVENTION

A photonic apparatus made from a stretchable and flexible material is provided. The apparatus may be a garment is especially suitable for wearing around, for example, the torso of a person. The garment provides a wearer with light therapy within a specific wavelength range, which replicates the beneficial natural light of the sun therein providing health benefits that may include treatment of various medical conditions. The garment may take the form of a blanket, wrap, belt, cape, vest, hood, cap, headband, shirt or the like. The light source may include light emitting diodes (LEDs), optical fibers or solid-state light emitting chips, which may be contained in a removable light transmitting pouch within the interior of the apparatus, so that the light may be powered by an internal power source to provide freedom of movement during treatment. In an embodiment, the light source is removably housed within the pouch wherein the pouch itself may be removed from the interior of the apparatus to be charged and replaced in the apparatus for wireless treatment use.

The removable pouch may also house a safety heat-dissipating technology so as to allow the pouch to directly contact the skin of the wearer without causing burns or other injury. A heat sink may be mounted onto the lighting apparatus to maximize the surface area and increase airflow to cool the lighting components. The heat sink may be made from a thermally efficient, lightweight material such as aluminum that allows heat to pass through it quickly. The heat sink may be fin-shaped to increase surface area, and the fins are aligned vertically with enough space between them to increase the natural convection process of the free flow of air over the lighting components.

The garment may wrap around the wearer in a secure fashion. The present apparatus design will direct substantially all the light onto the skin of the wearer, therein serving the dual purpose of both shielding the wearer's eyes from the light produced and preventing the wasteful dissipation of energy through ambient disbursement. The removable pouch may also be placed, for example, directly on the skin of the wearer and attached by disposable adhesive pads. The light emitting from the garment may be controlled by an operating system contained in a smart controller, which can be housed either inside or outside the pouch. As a safety measure, the light source may only be activated by the wearer once the garment is properly secured. In an embodiment, a smart controller may be integrated with an application, which may be run through a portable technology device (such as a smart phone) and may be used to individualize treatments, record use, and remind the wearer to use the device.

The present apparatus relates to a garment or wearable apparatus which may be used to transmit photonic energy in the form of light therapy specifically calibrated to replicate the beneficial wavelengths of sunshine. The apparatus is especially suitable for individuals who have conditions which may be treatable with phototherapy, photo-modulation, and light therapy as well as those who do not have access to sunshine including those that have low energy, low mood, ill health and low vitality, as well as healthy individuals desiring the benefits of sunshine.

The present apparatus utilizes an advanced light source, including light emitting diodes (LEDs), fiber optics, and low level intensity lasers in various beneficial wavelengths with distinct advantages over mercury lights such as using less energy, transmitting less heat, operating at precise wavelengths, and lasting substantially longer. The garment or wearable apparatus delivery system may allow for large surface treatment area and direct contact with the skin of the wearer. The device may be operated with an internal power source and controlled by a smart and customizable operating system that can integrate with a smart phone and other portable electronic devices. The efficacy of light therapy is dependent upon beneficial wavelength and combining beneficial wavelengths, irradiating the amount of surface area of the body that is treated, and the distance of the light source from the skin. The present apparatus optimizes all three factors that make light therapy efficacious while overcoming the limitations of the prior art in a portable, technologically advanced, user friendly device.

An advantage of the present light therapy apparatus is that the present light therapy apparatus provides light therapy in wavelengths that replicate the beneficial light of the sun that envelopes the user to maximize the energy at the skin, shields the eyes from ambient light, is portable so that it can be used without wires due to its internal power source, and is controlled by a smart, customizable, operating system. This application of the apparatus could be utilized for general health and wellness, optimizing mood, increasing energy, decreasing pain, decreasing disease risk, treating disease, and enhancing vitality.

Another advantage of the present light therapy apparatus is that the present light therapy apparatus provides photomodulation in wavelengths that deliver low level light therapy controlled by a smart, customizable, operating system for treatment of conditions of damaged tissue. This application of the apparatus may be utilized for treatment and prevention of conditions including but not limited to chronic pain, back pain, concussion, PTSD, and TBI.

Still another advantage of the present light therapy apparatus is that the present light therapy apparatus provides phototherapy in the specific wavelengths, which are appropriate for treatment of various medical conditions and skin disorders. This application of the apparatus may be utilized for treatment and prevention of conditions including but not limited to psoriasis, MS, Parkinson's disease, Alzheimer's disease, vitamin D deficiency, concussion, PTSD, TBI, cancer, general health and wellness, optimizing mood, increasing energy, and enhancing vitality.

Yet another advantage of the present light therapy apparatus is that the present light therapy apparatus is suitable for home use being constructed of soft, pliable, stretchable, washable material, which may be treated with proprietary nanotechnology coating that makes it impervious to water.

In an alternative embodiment, the present light therapy apparatus may be constructed for clinical use.

In still another alternative embodiment, the present light therapy apparatus may use disposable material for single use sessions.

And an advantage of the present light therapy apparatus is that the present light therapy apparatus may be made from a material treated with an anti-microbial coating for increased sanitation.

The garment or wearable apparatus may be constructed in the shape of a blanket, wrap, belt, cape, vest, cap, headband, hood or shirt. The garment or wearable apparatus envelops the user comfortably while delivering light therapy, phototherapy or photomodulation. The garment or wearable apparatus easily slips on the wearer, is adjustable in size, and secures in place, is lightweight and completely portable allowing the user complete freedom of movement during usage. The garment or wearable apparatus wraps around the wearer in a secure fashion and directs all the light onto the wearer's skin, serving the dual purpose of shielding the wearer's eyes from the light and not allowing the energy to be wasted through ambient disbursement. Due to the internal power source and functionality of the garment or wearable apparatus, normal activities may be performed during usage unlike other light therapy devices that require restricted activity due to user's need for close proximity to unit, external power source, and eye-sight restricting glasses.

The light source for the present apparatus, which may include light emitting diodes, optical fibers or solid-state light emitting surface mount diodes, may be contained in a removable light transmissive pouch which may be placed inside of the interior of the garment or wearable apparatus. Recent technological advancements allow the light therapy, phototherapy and photomodulation to be delivered in close proximity to the skin at a low intensity, low heat, with specific beneficial wavelengths. Short treatment times are possible due to the close proximity of the light transmission to the skin.

In one embodiment of the present light therapy apparatus, the present apparatus produces transmits light at wavelengths between about 630 nm to about 904 nm. In an alternative embodiment of the present apparatus, the apparatus transmits light at a wavelength between 298 nm and 315 nm. In still another embodiment, the light is transmitted as a monochromatic specific single wavelength. In yet another embodiment, the light transmitted by the apparatus encompasses multiple monochromatic specific single wavelengths. While in yet another embodiment, the light emitted from the apparatus is from broad band, narrowband, and or a combination of broad and narrow band wavelengths.

For decreased power consumption, improved heat dissipation, and increased life span of the light, as well as enhanced treatment options, a cycle process allows the present apparatus to alternately operate the lights while the unit is operating so that multiple wavelengths can be used in the device but operated at separate times from each other so as not to interfere with one another. Specifically, lights emitting wavelengths between about 630 nm to about 904 nm can be combined with lights emitting wavelengths between 298 nm and 315 nm, but operated separately within the same treatment session.

As stated above, the removable light source of the present apparatus may be housed in a removable pouch wherein the removable pouch may be removed from the garment. In particular, the removable pouch may be removed from the apparatus so that apparatus may be cleaned and so as to further allow charging of the internal power source.

The removable pouch may also house heat-dissipating technology so as to allow direct contact of the removable pouch with the skin of the wearer. The heat dissipating technology including a heat sink is mounted onto the lighting apparatus to maximize the surface area and increase airflow to cool the lighting components. The heat sink is made from a thermally efficient, lightweight material such as aluminum that allows heat to pass through it quickly. The heat sink is fin shaped to increase surface area, and the fins are aligned vertically with enough space between them to increase the natural convection process of the free flow of air over the lighting components.

The removable pouch may include a light transmissive layer on the inside surface (the surface closest to the skin of the wearer). The removable pouch may also be placed, for example, directly on the skin of the wearer and attached by disposable adhesive pads.

In an embodiment, the removable pouch may also connect to a wireless smart controller operating system, which will not activate until the garment or wearable apparatus is securely fastened. The operating system controls treatment time, restricts dosage to maximum allowed during time frame, and can be integrated into the device, and a smart phone to individualize treatments, record use, and remind the wearer to use.

External power source, internal batteries, rechargeable batteries or an AC plug may power the garment or wearable apparatus. All embodiments of the power source are removable from the garment or wearable apparatus to allow for washing of the garment or wearable apparatus and replacement of the lights and optional batteries. Once the pouch is charged, the internal power source provides for wireless usage and freedom of movement of the wearer.

For a more complete understanding of the above listed features and advantages of the light therapy apparatus reference should be made to the following detailed description of the preferred embodiments and to the accompanying drawings.

BRIEF DESCRIPTION OF THE DRAWINGS

FIG. 1 illustrates a front view of the photonic apparatus.

FIG. 2 illustrates a back view of the photonic apparatus wherein the removable pouch is in the process of being inserted within the interior of the photonic apparatus.

DETAILED DESCRIPTION OF A PREFERRED EMBODIMENT

A photonic apparatus made from a stretchable and flexible material is provided. The apparatus may be a garment is especially suitable for wearing around, for example, the torso of a person. The garment provides a wearer with light therapy within a specific wavelength range, which replicates the beneficial natural light of the sun therein providing health benefits that may include treatment of various medical conditions. The garment may take the form of a blanket, wrap, belt, cape, vest, hood, cap, headband, shirt or the like. The light source may include light emitting diodes (LEDs), optical fibers or solid-state light emitting chips, which may be contained in a removable light transmitting pouch within the interior of the apparatus, so that the light may be powered by an internal power source to provide freedom of movement during treatment. In an embodiment, the light source is housed within the pouch wherein the pouch itself may be removed from the interior of the apparatus to be charged and replaced in the apparatus for wireless treatment use.

Figure 6:
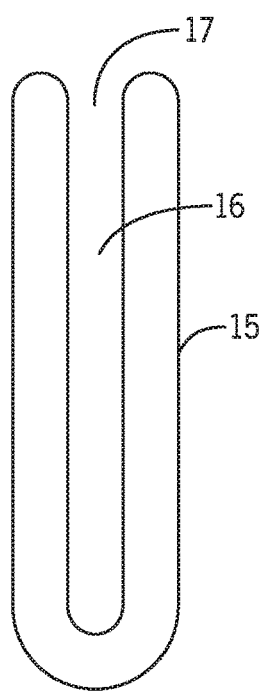
FIG. 6 illustrates a side view of the removable pouch of the photonic apparatus wherein the light emitting device is not in the removable pouch.
Figure 9:
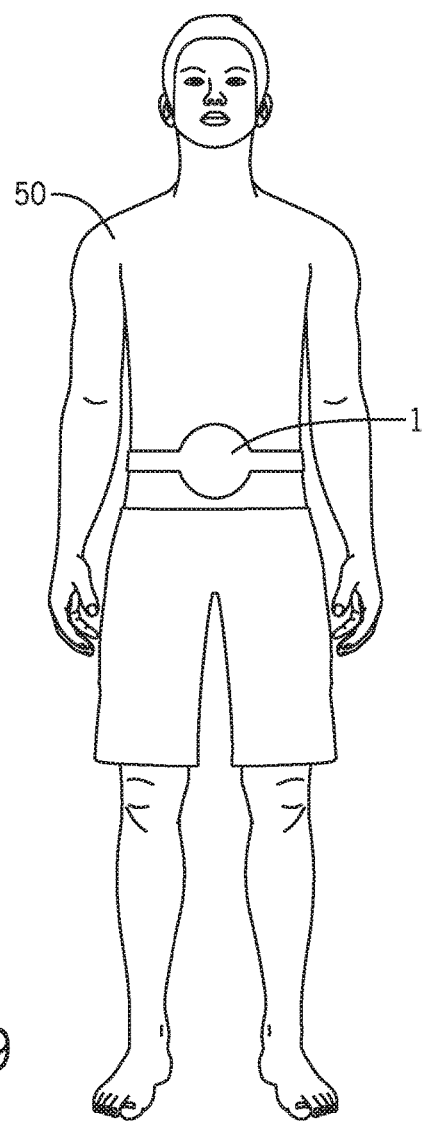
FIG. 9 illustrates a front view of a person wearing the photonic apparatus around his/her waist.

Referring first to FIGS. 1 and 2, in an embodiment, the present apparatus includes a photonic light apparatus 1. The photonic light apparatus 1 may be a portable garment which may be especially suitable for wearing. The photonic light apparatus 1 may have a housing having a front 2, a back 3, a first side 4, a second side 5, a top 6, a bottom 7 and an interior 8 (FIG. 6). The interior 8 may be a hollow compartment located approximately half way between the first side 4 and the second side 5 and wherein the hollow compartment is accessible from outside the device 1, as discussed below. The photonic light apparatus 1 is preferably portable and lightweight. In an embodiment, the photonic light apparatus 1 may be a garment capable of being worn by a person 50 (FIG. 9). FIG. 9 illustrates the photonic apparatus 1 being worn around the waist of a person 50, but it should be understood that the apparatus 1 may be worn anywhere on the body and may further be placed on the body so as to allow for phototherapy treatment virtually anywhere on the body. Preferably, the housing of the photonic light apparatus 1 (with the electrical components removed) is made from a washable material and thus capable of being washed in a standard washing machine. In an alternative embodiment, the electrical components (such as the LEDs 40) may be treated with a nanotechnology coating which allows any moisture or liquid to bead and roll off the electrical components and therein allows washing of the entire apparatus 1. In another alternative embodiment, photonic light apparatus is made from a disposable adhesive material for single use applications 1.

In an embodiment, the housing of the photonic apparatus 1 may be made from a transmissive or optic fiber material which may be form-fitted to the body of the person 50. Further, the apparatus 1 may have, for example, an adjustable hook and loop fastener system 25 (or clasps, buttons, or the like) which may allow the apparatus 1 to be properly secured around the body of the person 50 as opposed to if the person 50 merely wants the apparatus 1 to be loosely placed over a part of his/her body while relaxing and stationary. In an alternative embodiment, the first side 4 and the second side 5 have electrical couplings which require mating before the apparatus 1 will activate. As a result, the apparatus 1 may be not turn on without first being properly secured.

Figure 3:
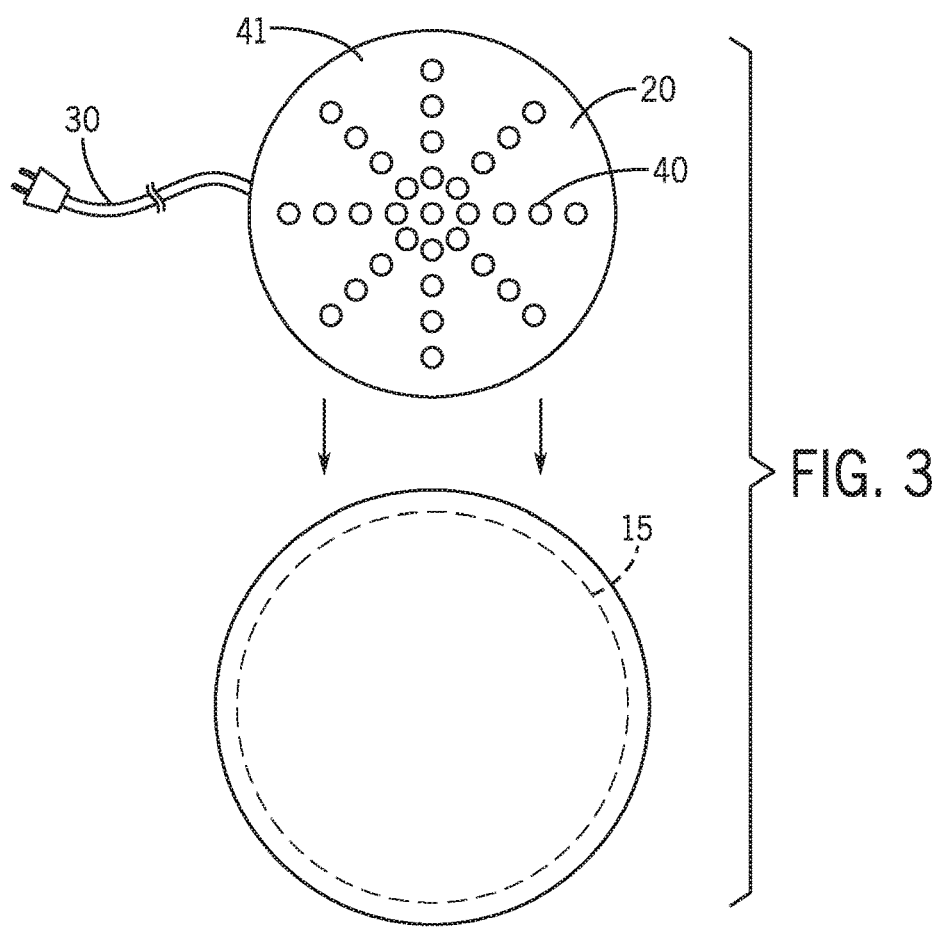
FIG. 3 illustrates a front view of the light emitting device contained in the removable pouch of the wearable photonic apparatus.
Figure 4:
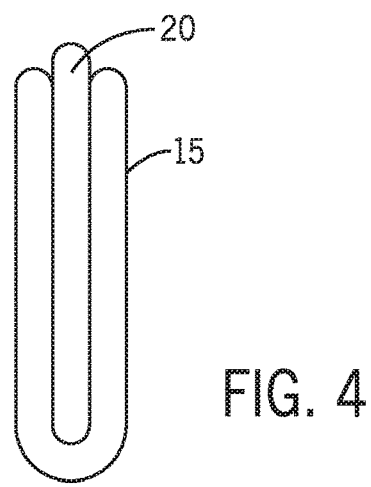
FIG. 4 illustrates a side view of the light emitting device contained in the removable pouch and placed within the interior of the apparatus.
Figure 5:
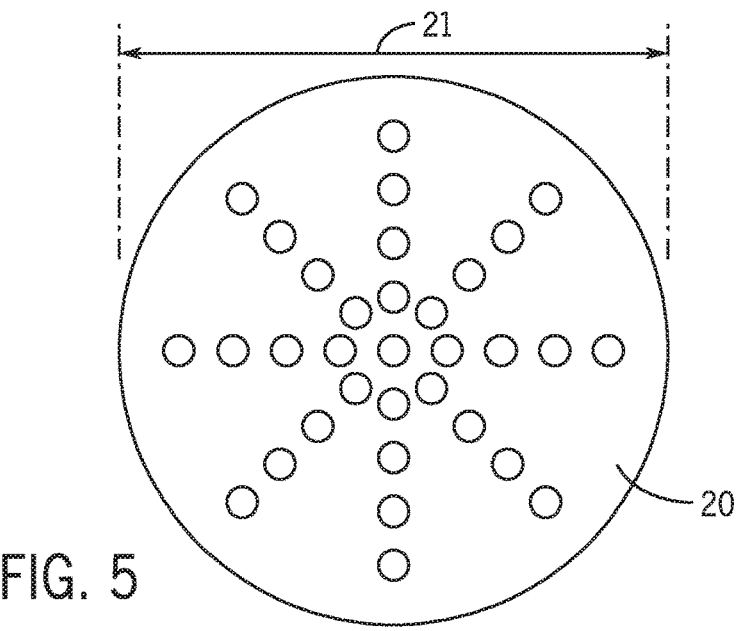
FIG. 5 illustrates a front view of the light emitting device of the apparatus contained in the removable pouch.

In an embodiment, a removable pouch 15 (FIG. 3) may be removably secured within the interior 8 of the housing. The removable pouch 15 may have an interior 16 (FIG. 6) for receiving a removable light emitting device 20. In an embodiment, the light emitting device 20 is made up of a plurality of lights such as, for example, LEDs 40 secured to a circular disk 41. Preferably, the removable pouch 15 and the light emitting device 20 are both circular in shape so as to maximize comfort while being worn by the person 50. The removable pouch 15 may have an opening slit 17 located at the top of the removable pouch 15 wherein the opening slit 17 receives the removable light emitting device 20. The opening slit 17 of the removable pouch 15 may therefore be slightly greater in size than a diameter 21 of the light emitting device 20 so that the light emitting device 20 may fit through the opening slit 17 of the removable pouch 15 to gain access to the interior 16 of the removable pouch 15. Further, the removable pouch 15 may itself be slightly smaller than an opening (not shown) on the top 6 of the apparatus 1 which receives the removable pouch 15.

In an embodiment, a power cord 30 (FIG. 3) may connect the removable light emitting device 20 to a power source (not illustrated) to charge the internal battery. The power source may be AC or DC. In an embodiment utilizing DC current, the battery may be, for example, a lithium ion rechargeable battery which may power the apparatus 1 allowing for the apparatus 1 to be portable and therefore, worn by the person 50 while the person 50 is mobile.

Figure 7:
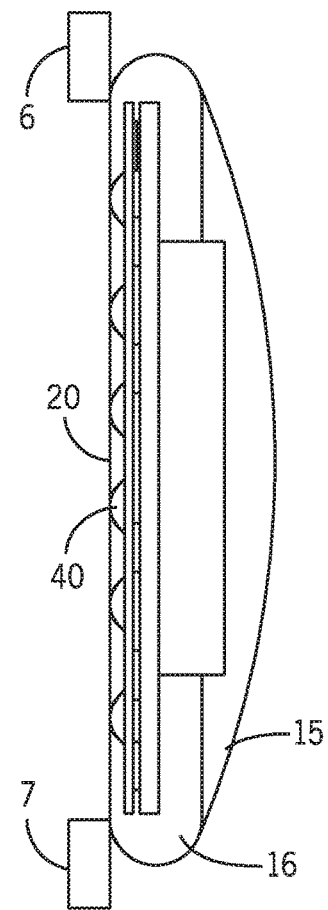
FIG. 7 illustrates a side view of the light emitting device located within the interior of the removable pouch.
Figure 8:
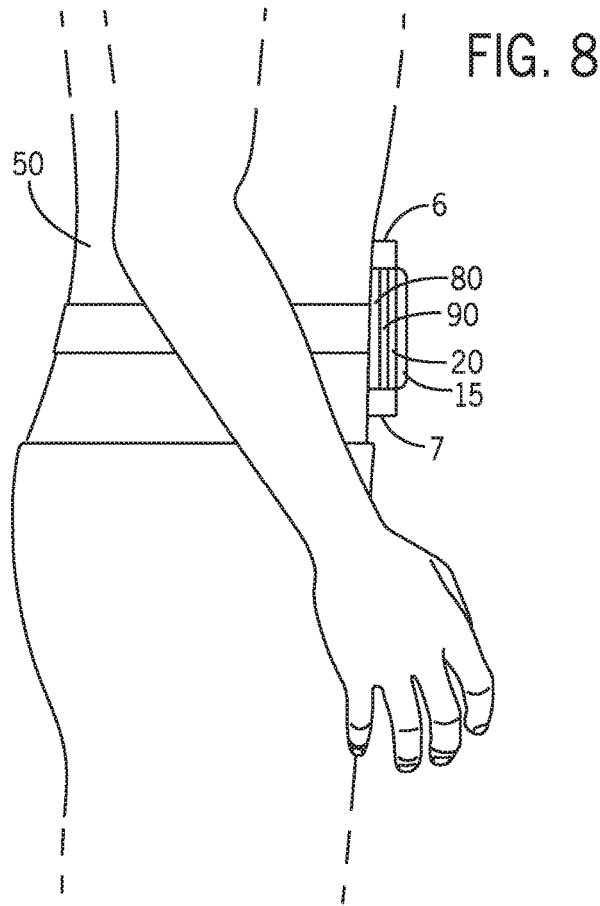
FIG. 8 illustrates a side view of the apparatus 1 being worn around the waist of a person.

Referring now to FIGS. 7 and 8, in an embodiment, the light emitting device 20 may shine through a transmissive layer 90 that protects the lights but allows the lights contained within the interior 16 of the removable pouch 15 to pass through it. In particular, the transmissive layer 90 (FIG. 8) may be located within the interior 16 of the removable pouch 15, and may be present between the light emitting device 20 and the skin of the person 50. As a result, the transmissive layer 90 may protect the light emitting device 20 but allow the light to pass through to the skin of the person 50.

Figure 13:
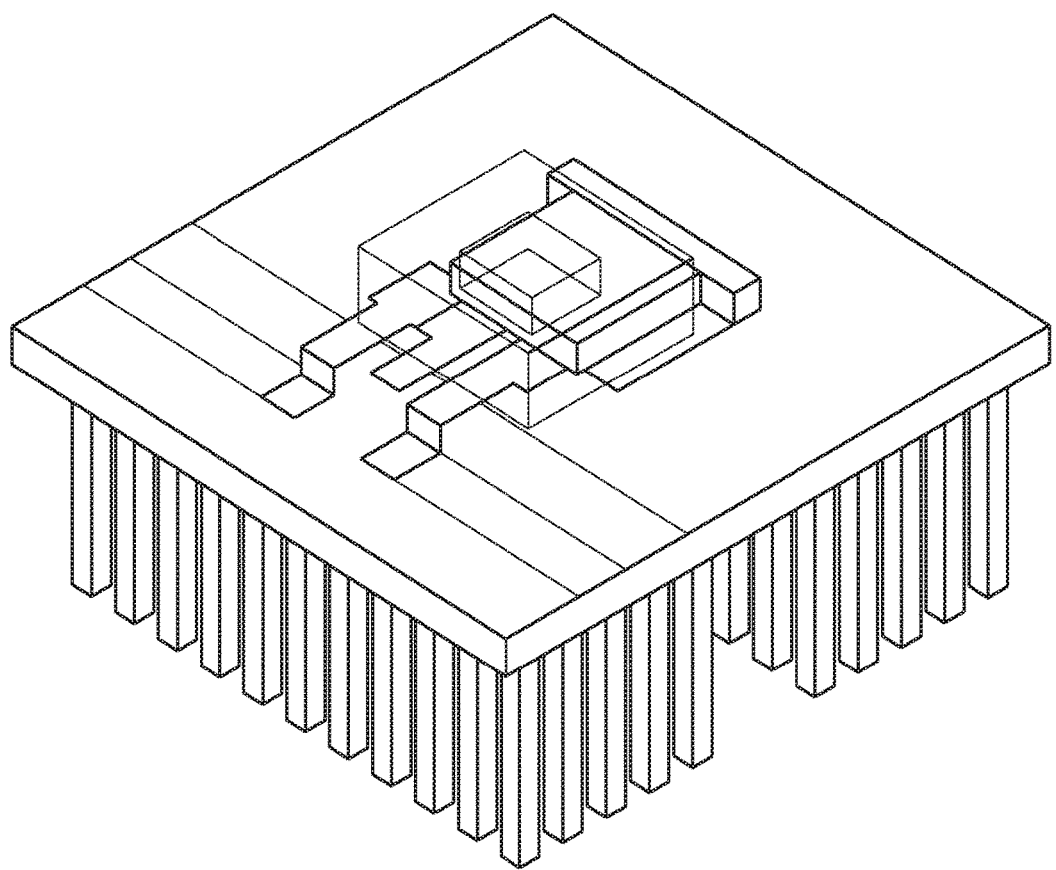
FIG. 13 illustrates a fin-shaped heat sink utilized with the lights to increase heat dissipation.

In an embodiment, the light emitting device 20 delivers light in close proximity to the skin of the person 50 at a low intensity, low heat, with specific beneficial wavelengths, which may include but are not limited to, 298 nm to 315 nm, and 630 nm to 940 nm. Heat dissipating technology may be included in the pouch to reduce heat from the light emitting device 20. In particular, a heat sink (FIG. 13) may be mounted onto the lighting apparatus to maximize the surface area and increase airflow to cool the lighting components. More specifically, each light may have a separate heat sink as illustrated in FIG. 13. The heat sink may be made from a thermally efficient, lightweight material such as aluminum that allows heat to pass through it quickly. The heat sink may be fin-shaped to increase surface area, and the fins are aligned vertically with enough space between them to increase the natural convection process of the free flow of air over the lighting components. Short treatment times are possible due to the close proximity of the light transmission to the skin of the person 50.

As stated above, the light emitting device 20 may contain a plurality of, for example, LEDs 40 which emit a wavelength or wavelengths suitable for treatment and prevention of various conditions including but not limited to vitamin D deficiency, MS, Alzheimer's disease, Parkinson's disease, cancer, concussion, PTSD, and TBI. In an embodiment, the arrangement of LEDs 40 may transmit light at wavelengths of 298 nm and in another embodiment, the LEDs 40 may transmit light at wavelengths at 308 nm. In another embodiment, the LEDs 40 may transmit light 40 within a narrow band UVB wavelengths ranging from 298 to 315 nm therein optimizing the beneficial wavelengths of the UVB spectrum. In still another embodiment, the LEDs 40 may transmit light at wavelengths from 630 nm to about 904 nm optimized for damaged tissue treatment including but not limited to conditions such as pain, traumatic brain injury, concussion and post-traumatic stress disorder.

Figure 12:
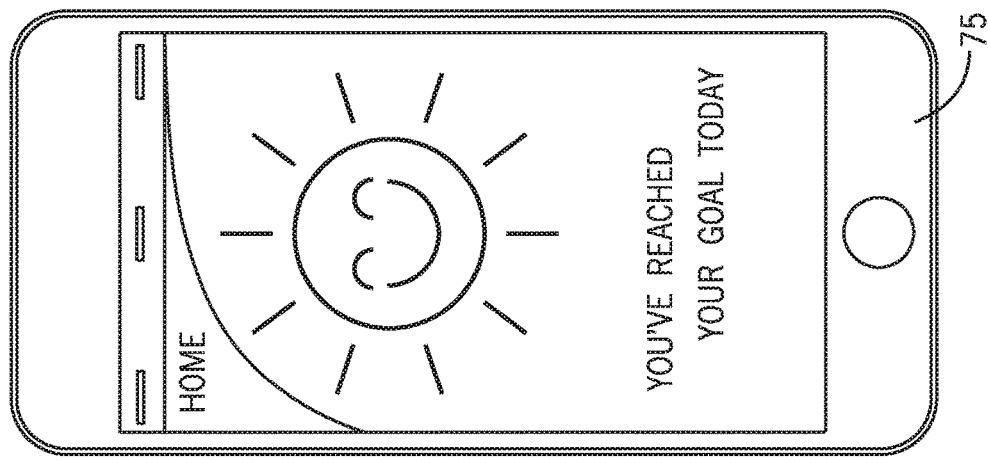
FIG. 12 illustrates a view of a smartphone application displaying that a phototherapy session is completed.
Figure 11:
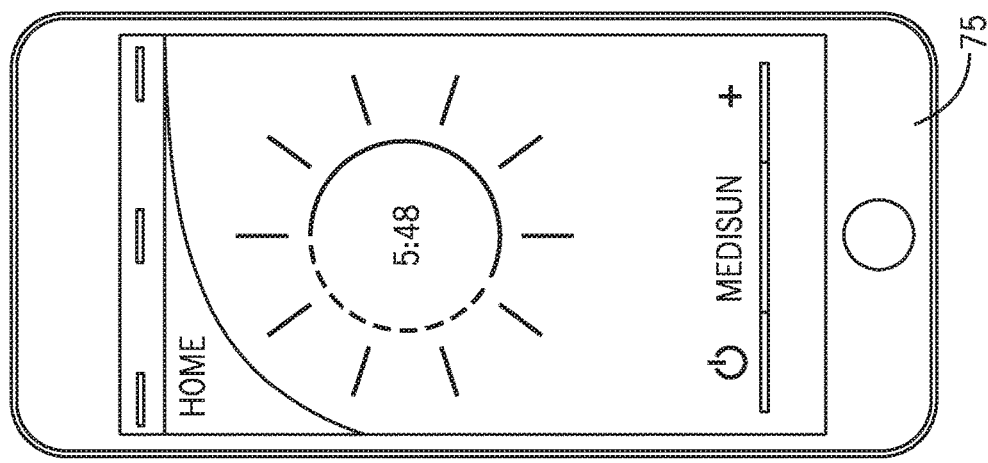
FIG. 11 illustrates a view of a smartphone application displaying that a phototherapy session is approximately half-way finished.
Figure 10:
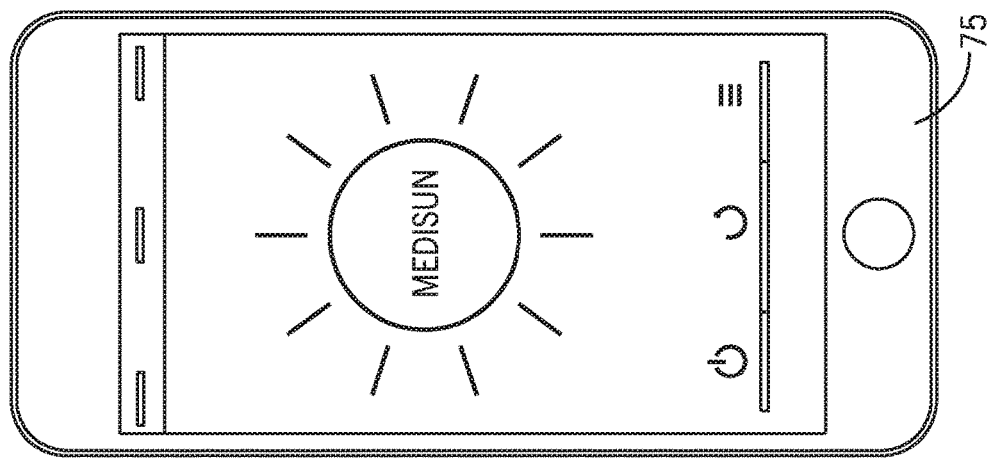
FIG. 10 illustrates a view of a smartphone application displaying that a phototherapy session has just started.

In a present embodiment of the apparatus 1 the LEDs 40 may be arranged over the torso of the person 50 to provide illumination over a large portion of the skin of the person 50. The LEDs 40 may be activated by an operating system contained in a smart controller or integrated into an electronic device 75 (FIGS. 10-12). The controller may allow some of the LEDs 40 to provide light while other LEDs 40 remain temporarily dormant and in stand-by mode for decreased power consumption, improved heat dissipation, and increased life span of the light emitting device 20, as well as enhanced treatment options. The light emitting device 20 may be charged with external power cords 30 prior to using, so that person 50 may use the apparatus 1 wirelessly. In an embodiment, the person 50 may plug in the apparatus 1 via AC current while the person 50 is stationary and near an outlet.

Referring now to FIGS. 10-12, in an embodiment, the apparatus 1 may connect to a smart controller operating system installed on an electronic device 75. In an embodiment, the electronic device 75 may wireless control the light emitting device 20. The apparatus 1 may not be activated until the garment or wearable apparatus is securely fastened around the person 50. In particular, as stated above, the first side 4 and the second side 5 may need to be connected (via the fastener 25) for the apparatus 1 to operate. The operating system may control the treatment time and may restrict dosage to a maximum allowed during the time frame, and can be integrated directly into the device and into a smart phone to individualize treatments, record use, and remind the wearer to use.

Referring now to FIG. 8, in an embodiment, a user may secure the apparatus 1 around, for example, his or her waist. The front 2 of the apparatus 2 may have an opening window 80 that exposes the interior compartment 8 and that allows the light emitting device 20, which faces the skin of the person 50 to direct the light directly at the person 50. As a result, virtually all of the light contacts the skin of the person 50 and is prevented from accidently reaching the eyes or other sensitive areas of the person 50. In an embodiment, the back 3 of the device 1 may lack an opening window 80. Further, in an embodiment, the opening window 80 of the apparatus 1 may have a diameter which is less than the diameter 21 of the light emitting device 20 and less than the diameter of the removable pouch 15 such that the light emitting device 20 and removable pouch 15 remain secured within the interior 8 of the apparatus 1.

Although embodiments of the present invention are shown and described therein, it should be understood that various changes and modifications to the presently preferred embodiments will be apparent to those skilled in the art. Such changes and modifications may be made without departing from the spirit and scope of the present invention and without diminishing its attendant advantages. It is, therefore, intended that such changes and modifications be covered by the present application.

I claim:

1. A photonic wearable assembly comprising:
   a housing have a top, a bottom, a first side, a second side, a front, a back and a hollow interior compartment;
   a first securing mechanism having a first electrical coupling located at the first side of the housing and a corresponding second securing mechanism having a second electrical coupling located at the second side of the housing wherein the first securing mechanism and the second securing mechanism may be temporarily secured together and wherein the housing is configured to be worn around a waist of a person; and
   a removable photonic device which delivers light wherein the removable photonic device is temporarily secured within the hollow interior compartment;
   an opening window located on the front of the housing wherein the opening window exposes the hollow interior compartment and wherein the back of the housing is solid;
   wherein the removable photonic device is capable of delivering light therapy to skin of a person; and
   wherein the first securing mechanism of the first side and the second securing mechanism of the second side of the housing must be electrically secured together in order for the removable photonic device to deliver light.

2. The photonic wearable assembly of claim 1 wherein the hollow interior compartment is circular.

3. The photonic wearable assembly of claim 1 wherein the removable photonic device is circular.

4. The photonic wearable assembly of claim 1 wherein the hollow interior compartment is located approximately half way between the first side and the second side of the housing.

5. The photonic wearable assembly of claim 1 further comprising:
   a removable pouch having a hollow interior wherein the removable pouch temporarily receives the removable photonic device and wherein the removable pouch and the removable photonic device together may be temporarily secured within the hollow interior compartment of the housing.

6. The photonic wearable assembly of claim 1 further comprising:
   a transmissive layer located within the opening window.

7. The photonic wearable assembly of claim 1 further comprising:
   a heat sink secured to the removable photonic device wherein the heat sink device is capable of dissipating heat generated from a light of the removable photonic device.

8. The photonic wearable assembly of claim 7 wherein the heat sink is fin-shaped.

9. The photonic wearable assembly of claim 1 further comprising:
   a remote electronic device wherein the remote electronic device is in wireless communication with the removable photonic device and wherein the remote electronic device is capable of allowing a user to control the removable photonic device.

10. The photonic wearable assembly of claim 1 wherein the photonic device is capable of providing light to the skin of a person between 298 nm to 315 nm or 630 nm to 940 nm weighlengths.

11. The photonic wearable assembly of claim 1 wherein the front of the housing has a window for allowing light to pass through and wherein the back of the housing lacks a window for allowing light to pass through.

* * * * *